United States Patent [19]

Rembaum et al.

[11] 3,985,632

[45] Oct. 12, 1976

[54] SMALL, POROUS POLYACRYLATE BEADS

[75] Inventors: Alan Rembaum; Shiao-Ping Siao Yen; William J. Dreyer, all of Altadena, Calif.

[73] Assignee: California Institute of Technology, Pasadena, Calif.

[22] Filed: Oct. 4, 1974

[21] Appl. No.: 512,111

Related U.S. Application Data

[62] Division of Ser. No. 434,124, Jan. 17, 1974.

[52] U.S. Cl. .................. 204/159.15; 204/159.22; 260/2.5 B; 260/874; 260/101
[51] Int. Cl.² ................... C08F 8/00; C08F 226/00
[58] Field of Search .............. 204/159.22, 159.23, 204/159.24, 159.15; 260/86.1 E, 86.1 N, 215 B, 80.73, 80.75

[56] References Cited
UNITED STATES PATENTS 3,663,467  5/1972  Albright .......................... 260/2.5 B
3,699,089  10/1972  Wichterle ....................... 260/86.1 E
3,767,600  10/1973  Albright .......................... 260/2.2 R

*Primary Examiner*—Richard B. Turer
*Attorney, Agent, or Firm*—Marvin E. Jacobs

[57] ABSTRACT

Uniformly-shaped, porous, round beads are prepared by the co-polymerization of an acrylic monomer and a cross-linking agent in the presence of 0.05 to 5% by weight of an aqueous soluble polymer such as polyethylene oxide. Cross-linking proceeds at high temperature above about 50°C or at a lower temperature with irradiation. Beads of even shape and even size distribution of less than 2 micron diameter are formed. The beads will find use as adsorbents in chromatography and as markers for studies of cell surface receptors.

13 Claims, No Drawings

SMALL, POROUS POLYACRYLATE BEADS

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

This is a division of application Ser. No. 434,124, filed Jan. 17, 1974.

BACKGROUND OF THE INVENTION

1. Field of the Invention

The present invention relates to uniformly-sized, porous, small, round, hydrophilic polymeric beads and methods of making the beads and to the use of the beads in separation of molecules and in various analytical and diagnostic techniques.

The invention is directed to particles and the methods by which they are made and does not include tracer tagging or biological and clinical application tagging aspects disclosed and claimed in copending U.S. patent application Ser. No. 177,017, filed Sept. 1, 1971, by William J. Dreyer.

2. Description of the Prior Art

There is a need for small, stable, spherical particles which are bio-compatible, i.e., do not interact non-specifically with cells or other biological components and which contain functional groups to which specific proteins and other bio-chemical molecules can be covalently bonded by established chemical procedures. Poly HEMA, a polyhydroxyethylmethacrylate, also known under the name Hydrogel, has been shown to possess blood compatible properties and is also used in the manufacture of contact lenses. The hydroxyl groups can be activated by cyanogen bromide for covalent bonding of proteins and other chemicals containing amino groups to the polymeric latex. Methacrylic acid residues which impart a negative charge onto the particles tend to prevent non-specific binding to cell surfaces and to provide carboxyl groups to which a variety of bio-chemical molecules can be covalently bonded using the carbodiimide method. Cross-linking of the polymeric matrix is essential to maintain the stability and size of the particles in both aqueous solution and in organic solvents commonly used in the fixation and dehydration of biological specimens for light and electron microscopy.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and differences in normal and tumor cell surfaces. In previous studies, the localization of antigens and carbohydrate residues on the surface of cells, notably red blood cells and lymphocytes, has been determined by bonding antibodies or lectins to such macromolecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently commercially available polystyrene latex particles have been utilized as immunologic markers for use in the SEM technique. The surface of such polystyrene particles is hydrophobic and hence certain types of macromolecules such as antibodies are adsorbed on the surface under carefully controlled conditions. However, such particles stick non-specifically to many surfaces and molecules and this seriously limits their broad application. These particles are uncharged and are not capable of any ionic or covalent bonding of protein and other biological molecules.

HEMA particles possess chemical groups suitable for covalent bonding. However, homopolymers of HEMA are generally too soft for formation of porous beads and conventional suspension polymerization techniques are found to form fairly large particles on the order of 40 to 60 microns. Red blood cells and lymphocytes have a size of the order of 8 to 10 microns and in order to bind to specific receptor sites the beads must be of an order of magnitude smaller than the biological cell.

Small, uniformly-sized, cross-linked, porous, polyacrylic beads will also find use as a low-cost, stable adsorbent in separating and purifying organic and inorganic compounds including polymers. The beads will also find use in chromatographic separation, filtration and gel permeation and affinity chromatography.

The hydrophilic organic gels commonly used in chromatography are sparsely cross-linked xerogels with a high swellability capacity in the eluent. They are characterized by considerable capacity ratio. However, the mechanical strength of the particles in the swollen state rapidly decreases with decreasing density of the cross-links. Application of the eluent under pressure at the column inlet frequency leads to plugging. Therefore, these gels are not suitable for highspeed gel chromatography. A new hydrophilic packing for gel chromatography is needed exhibiting high mechanical and hydrolytic stability.

SUMMARY OF THE INVENTION

In accordance with the invention, small, round, porous beads of uniformly small diameter are provided. The beads are formed from an acrylic monomer containing a hydroxy group. The beads are hydrolytically stable and of sufficient mechanical strength to be useful as an adsorbent in separating and purifying organic and inorganic compounds and will find use in column or in film chromatography, gel filtration and permeation, separation and analysis. The beads are of well characterized structure and of outstanding purity.

Small spheres covalently bonded to antibodies and other biological materials are useful as specific cell surface markers for scanning electron microscopy. The particles are found to bind to hormones, toxins, lectins and other molecules and have application in the detection and localization of a variety of cell surface receptors. Particles tagged with fluorescent dye or radioactive molecules serve as sensitive markers for fluorescent microscopy and as reagents for quantitative study of cell surface components by covalently bonding lectins, antigens, hormones and other molecules to these spheres, the detection and localization of specific carbohydrate residues, antibodies, hormone receptors and other specific cell surface components can also be determined. These reagents also have applications in highly sensitive radioimmune assays as visual markers for light, fluorescent and transmission electron microscopy, for radioactive quantitation of specific cell surface receptors and as potential therapeutic reagents.

Uniformly-shaped, porous, round beads are prepared by co-polymerization of an acrylic monomer and a cross-linking agent in the presence of 0.1 to 5%, preferably 0.2 to 2%, by weight of an aqueous soluble polymer such as polyethylene oxide. Cross-linking proceeds at high temperature above about 50° C or at a lower temperature with irradiation. Beads of even shape and even size distribution of less than 2 micron diameter are formed. The beads will find use as adsorbents in chromatography and as markers for studies of cell surface receptors.

These and other objects and many attendant advantages of the invention will become apparent as the description proceeds.

DESCRIPTION OF THE PREFERRED EMBODIMENTS

The beads are prepared by the aqueous suspension polymerization of a monounsaturated, hydroxy substituted, liquid acrylic monomer and a cross-linking agent in the presence of 0.1 to 5% of a water soluble polymeric suspending agent. Polymerization proceeds at a temperature above about 50° C, preferably 70° C to reflux in the presence or absence of a catalyst or at a lower temperature of −70° C to 70° C with application of high energy radiation to the polymerizable mixture.

The monomer is suitably a hydroxy alkyl substituted acrylate or acrylamide or an amino alkyl substituted acrylate. Representative monomers may be selected from compounds of the formula:

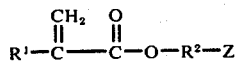

where $R^1$ is hydrogen or lower alkyl of 1–8 carbon atoms, $R^2$ is alkylene of 1–12 carbon atoms, Z is OH or

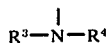

where $R^3$ or $R^4$ are H, lower alkyl or lower alkoxy. Hydroxyethylmethacrylate, hydroxypropyl methacrylate, dimethylaminoethyl methacrylate and 2-aminoethyl methacrylate are readily available commercially. Minor amounts of 1–35%, suitably 10–25%, of a compatible comonomer such as a lower alkyl methacrylate, acrylic or methacrylic acid, styrene or vinyl toluene may be present in the polymerizable mixture.

The cross-linking agent is present in the polymerizable mixture in an amount from 0.1 to 30% and is a liquid polyunsaturated compound such as diene or a triene capable of addition polymerization with the unsaturated group of the monomer. Suitable compounds are low molecular weight liquid polyvinyl compounds such as ethylene dimethacrylate, divinyl benzene, trimethylol propane trimethacrylate and N,N'-methylene-bis-acrylamide.

A commerical form (94%) of hydroxyethylmethacrylate (HEMA) and hydroxypropyl methacrylate (HPMA) as supplied, contains small amounts of methacrylic acid, hydroxyalkoxyalkylmethacrylate and dimethacrylates - ethylene dimethacrylate in HEMA and propylene dimethacrylate in HPMA. HPMA is generally a mixture in which the principle monomers comprise 68–75% of 2-hydroxypropyl and 25–32% of 1-methyl-2-hydroxyethylmethacrylate. Typical compositions in weight percentage follow:

| Compound | HEMA - 94% | HPMA - 94% |
| --- | --- | --- |
| Hydroxyalkylmethacrylate | 86 | 87 |
| Higher boiling methacrylate, principally hydroxyalkoxy-alklymethacrylate | 6 | 5 |
| Methacrylic Acid | 3.5 | 4.5 |
| Dimethacrylate | 1.5 | 0.7 |

The monomers are diluted in aqueous medium at a level of from 5 to 50% by weight. The aqueous medium comprises water and the water soluble polymer. The water soluble polymer may be present in an amount as low as 0.05 weight percent. Amounts above 5% are believed unnecessary and require added time and effort to remove the polymer from the final beads.

Finely and uniformly shaped and sized beads have consistently been produced in an aqueous medium containing a polyether. The polyethers generally have a molecular weight from 300,000 to 10,000,000, preferably 400,000 to 6,000,000, and are polymers of alkylene oxides such as ethylene oxide, propylene oxide or their mixtures. Polyethylene oxides are preferred due to their solubility in water.

The polymerization proceeds without catalyst and without stirring with application of heat to the mixture at a temperature of from 70° C to reflux, generally about 100° C or with application of high energy radiation capable of generating free radicals and initiating polymerization and forming cross-linking bonds between olefinic groups. Polymerization proceeds by application of 0.05 to 1.0 megarads of radiation from a cobalt gamma source at a temperature of 0° to 70° C. The reaction is preferably conducted under oxygen excluding conditions, generally by applying vacuum to the reaction vessel or by displacing the head space with an inert gas such as nitrogen. A free radical catalyst such as ammonium persulfate and additional agents such as other suspending or emulsifying agents may be present in the polymerizable mixture.

After polymerization has proceeded to completion, the polymerization mixture is diluted with hot water and filtered and washed with boiling water to remove the polyether. The dry material in over 90% yield is in the form of separate round beads or agglomerates of beads. Agglomerates, if present, are subdivided into beads mechanically by dispersion in a non-solvent liquid, crushing or grinding. The beads are uniformly sized and at least 80% and preferably at least 90% of the beads are of a uniform diameter less than 5 microns, preferably from 0.001 to 2 microns. The cross-linked porous beads are insoluble and swellable in water and are insoluble in common inorganic and organic solvents.

Specific examples of practice follow.

EXAMPLE 1

Commercial 94% HEMA containing 1.5 weight percent ethylene dimethacrylate and 0.5% hydroquinone as a stabilizer was vacuum distilled at 97°–99° C at a pressure of 1 mm Hg. 14 g of the freshly distilled HEMA was dissolved in 180 g of water. 4 g of a polyethylene oxide polymer of a molecular weight of about 4,000,000 was added and the mixture heated at mild reflux (98° ± 2° C) for 24 hours. The polymerized material was then diluted with hot water and filtered through a wire mesh. The separated solid on the wire mesh was washed with boiling water until the polyethylene oxide was removed. The dry material in a yield of over 90% was ground into individual beads, 80% of which had a diameter of 2 microns.

EXAMPLE 2

A mixture of 200 g of freshly vacuum distilled HEMA, 4 g of $1 \times 10^6$ molecular weight polyethylene oxide and 30 g of trimethylol propane trimethacrylate was diluted to one liter with water and nitrogen inerted. 0.1 megarad of radiation was applied to the mixture at room temperature from a cobalt gamma source over a period of about 15 minutes. The beads were filtered, washed with boiling watr several times and centrifuged to provide a 99% yield.

Under scanning electron microscope the dry beads were determined to be round and at least 90% were of a 1.6 micron diameter.

EXAMPLE 3

The following aqueous mixture was prepared.

| Component | Weight % |
| --- | --- |
| HEMA (Freshly distilled containing 1.5% ethylene dimethacrylate) | 16 |
| Trimethylol propane trimethacrylate (TPT) | 0.6 |
| Polyethylene oxide (M.W. $10^6$) | 0.4 |
| Dimethylaminoethyl methacrylate | 4.0 |

The mixture was nitrogen inerted and 0.1 megarads of radiation was applied to the mixture at room temperature from a cobalt gamma source for 15 minutes. The beads were recovered and separated as in Example 2 in 99% yield. Under scanning electron microscope, the diameter of over 90% of the beads was determined to be from 1–2 microns. The copolymer beads contain hydroxyl as well as dimethylamino groups. The procedure was repeated at 0° C in ice bath with 0.2 megarads over a period of 30 minutes with the same results.

EXAMPLE 4

The following aqueous mixture was prepared.

| Component | Weight % |
| --- | --- |
| Acrylamide | 20.6 |
| N,N'-methylene-bis-acrylamide | 0.6 |
| Polyethylene oxide (M.W. $10^6$) | 0.4 |

The mixture was polymerized under the conditions of Example 3 to yield agglomerated beads which were subdivided into individual beads having a diameter from 1–2 microns.

EXAMPLE 5

The following aqueous mixture was prepared.

| Component | Weight % |
| --- | --- |
| Dimethylaminoethyl methacrylate | 20.6 |
| TPT | 0.6 |
| Polyethylene oxide (M.W. $10^6$) | 0.4 |

The mixture was nitrogen inerted and subjected to 0.1 megarad of cobalt gamma radiation for 15 minutes. Individual beads of 1–2 micron diameter were produced.

The small, pure, round, uniformly-sized beads of this invention can be utilized for the labeling of biological cells such as lymphocytes. A diseased condition can be diagnosed by binding an antibody to beads, mixing the beads with a body serum and observing whether the beads bind to specific antigen sites causing precipitation or agglutination. The presence of OH, COOH and amine groups on the beads permits covalent bonding of biomolecules such as haptens, enzymes, antibodies or lectins to the beads by means of cyanogen bromide, carbodiimide or glutaraldehyde reactions. Diagnosible conditions are hepatitis, gonorrhea, rheumatoid arthritis, streptococcus infections, and pregnancy. Labeled beads may also be used for blood typing.

The beads also bind fluorescent dyes and will find use in fluorescent microscopy. Since the dye is bound to the bead particle and not to the antibody, a high degree of tagging can be attained without adversely affecting the antibody activity for studies requiring high sensitivity. The fluorescent dye bound beads can also act as a marker for cells by adding the beads to cells, in vitro or in vivo, and the attachment to specific cells observed.

EXAMPLE 6

0.2 g of the beads of Example 2 were suspended in 20 ml of $H_2O$, homogenized in a glass homogenizer and transferred to a beaker. 0.8 g of cyanogen bromide was added while stirring. The pH was maintained at 10–11 by addition of 2N NaOH. 5 mg of epsilon dansyl lysine was added and stirring continued for 1 hour. The mixture was centrifuged 6 times with distilled water. The supernatant liquid was not fluorescent after the sixth centrifugation. Highly fluorescent beads were recovered as determined by fluorescent microscopy.

EXAMPLE 7

0.1 g of 9-amino acridine hydrochloride were bound to 0.2 g of the beads of Example 2 following the procedure of Example 6. The beads were highly fluorescent.

Due to the hydrophilic and purity characteristics of the porous, round, finely-sized beads, the beads will also find use in affinity chromatography, column or thin film chromatography, gel filtration or permeation. The beads are capable of purification of highly charged synthetic and natural polyelectrolytes and can be used to separate both organic and inorganic molecules.

It is to be realized that only preferred embodiments of the invention have been described, and that numerous substitutions, alterations and modifications are all permissible without departing from the spirit and scope of the invention as defined in the following claims.

What is claimed is:

1. A method of preparing uniformly-shaped, porous, round beads having an average diameter below 2 microns comprising the steps of:
   copolymerizing a polymerizable mixture of an amino- or hydroxy-substituted acrylic monomer and a minor amount of a polyunsaturated cross-linking agent in aqueous medium containing 0.05 to 5% by weight of an aqueous soluble polyether by applying high energy radiation to the mixture; and recovering said beads.

2. A method according to claim 1 in which the polyether is a polyalkylene oxide having a molecular weight from 300,000 to 10,000,000 and is present in the polymerizable mixture in an amount from 0.2 to 2% by weight.

3. A method according to claim 2 in which the polyether is a polymer of ethylene oxide, propylene oxide or mixtures thereof and the molecular weight is from 400,000 to 6,000,000.

4. A method according to claim 2 in which polymerization is conducted at a temperature from $-70°$ C to reflux and at least 80% of the beads produced have a diameter of no more than 2 microns.

5. A method according to claim 1 in which the polymerization is conducted at a temperature of 0° to 70° C with application of 0.05 to 1.0 megarads of radiation to the mixture from a cobalt gamma source.

6. A method according to claim 2 in which the acrylic monomer is selected from a hydroxy substituted acrylate, an amino substituted acrylate, or mixtures thereof.

7. A method according to claim 6 in which the monomer is selected from compounds of the formula:

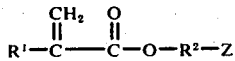

where $R^1$ is hydrogen or lower alkyl of 1–8 carbon atoms, $R^2$ is alkylene of 1–12 carbon atoms, Z is OH or

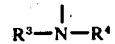

where $R^3$ or $R^4$ are H, lower alkyl of 1–10 carbon atoms or lower alkoxy of 1–10 carbon atoms.

8. A method according to claim 7 in which the monomer is selected from hydroxyethylmethacrylate, hydroxypropylmethacrylate, dimethylaminoethylmethacrylate and 2-aminoethylmethacrylate.

9. A method according to claim 6 in which the polymerizable mixture contains 1–35 weight percent based on said acrylic monomer of a comonomer selected from a lower alkyl methacrylate, acrylic acid, methacrylic acid, styrene or vinyl toluene.

10. A method according to claim 6 in which the cross-linking agent is present in the polymerizable mixture in an amount from 0.1 to 30% and is a liquid polyunsaturated compound.

11. A method according to claim 10 in which the cross-linking agent is a low molecular weight liquid polyvinyl diene or triene compound.

12. A method according to claim 11 in which the cross-linking agent is selected from ethylene dimethacrylate, divinyl benzene, trimethylol propane trimethacrylate, and N,N'-methylene-bis-acrylamide.

13. A method according to claim 7 in which the monomer is hydroxyethylmethacrylate.

* * * * *